US00PP14434P39

(12) United States Plant Patent
Weeks

(10) Patent No.: US PP14,434 P3
(45) Date of Patent: Dec. 30, 2003

(54) GRANDIFLORA ROSE PLANT NAMED 'WEZLAVN'

(50) Latin Name: *Rosa hybrida*
Varietal Denomination: cv. Wezlavn

(75) Inventor: O. L. Weeks, Chino, CA (US)

(73) Assignee: CP (Delaware), Inc., Wilmington, DE (US)

( * ) Notice: Subject to any disclaimer, the term of this patent is extended or adjusted under 35 U.S.C. 154(b) by 12 days.

(21) Appl. No.: 10/199,059

(22) Filed: Jul. 22, 2002

(65) Prior Publication Data

US 2002/0174464 P1 Nov. 21, 2002

Related U.S. Application Data

(63) Continuation of application No. 09/756,736, filed on Jan. 10, 2001, now abandoned.

(51) Int. Cl.[7] ..... A01H 5/00
(52) U.S. Cl. ..... Plt./138
(58) Field of Search ..... Plt./138

*Primary Examiner*—Bruce R. Campell
*Assistant Examiner*—Susan B. McCormick
(74) *Attorney, Agent, or Firm*—Burns, Doane, Swecker & Mathis, L.L.P.

(57) ABSTRACT

A new and distinct variety of Grandiflora rose plant is provided which forms attractive double blossoms that are light to medium lavender in coloration. The plant exhibits a bushy and well balanced growth habit, and good disease resistance. Medium green semi-glossy foliage is formed. The new plant growth commonly assumes a deep burgundy appearance. The new variety is particularly well suited for growing as attractive ornamentation in the landscape such as in parks and gardens. Cut flower production also is possible.

1 Drawing Sheet

Figures 1, 2, 3, 4, 5, 6, 7, 8, 9, 10, 11, 12, 13, 14, 15, 16, 17:
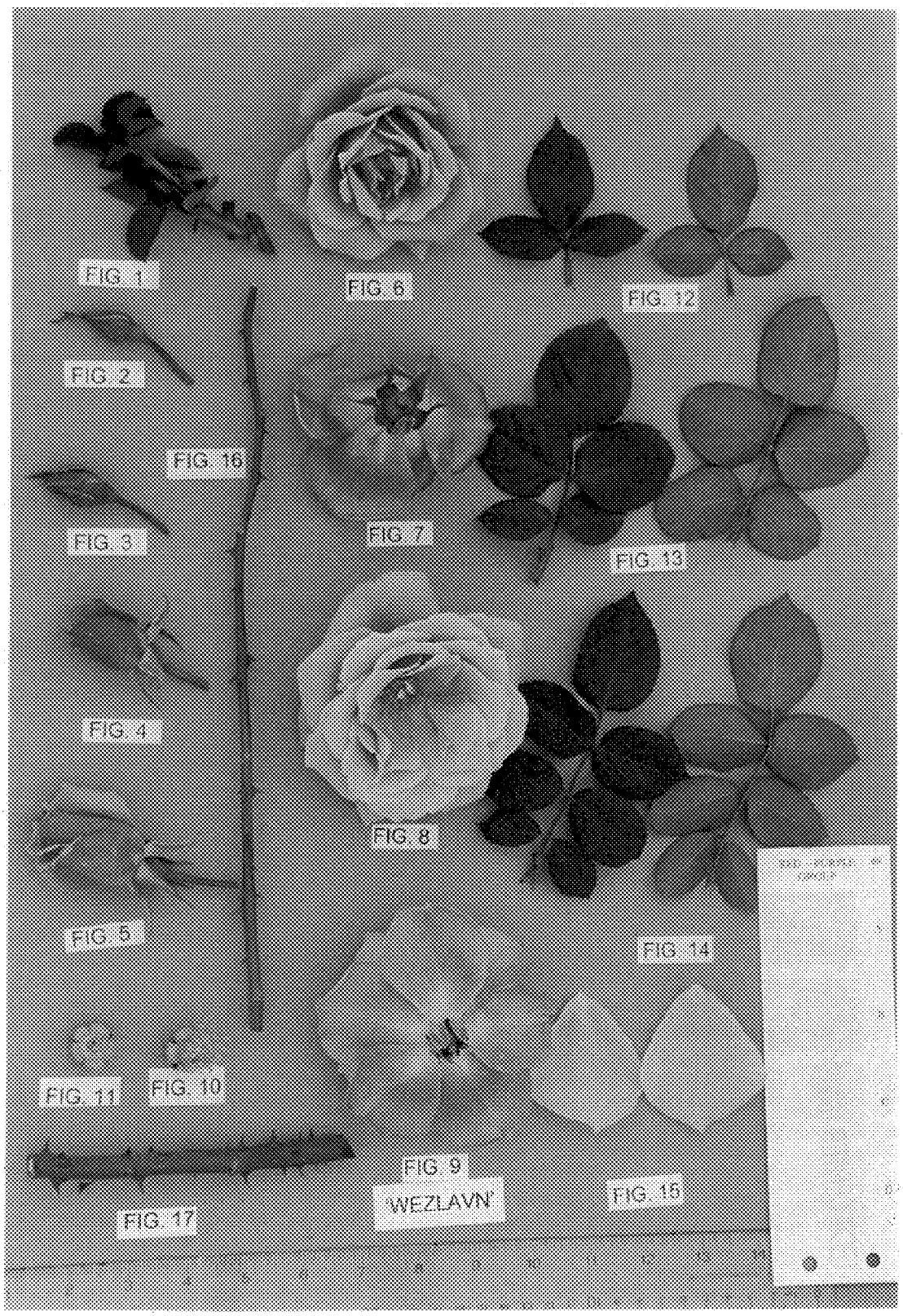

Botanical/commercial classification: Rosa hybrida/Grandiflora Rose Plant.
Varietal denomination: cv. 'Wezlavn'.

SUMMARY OF THE INVENTION

The new variety of *Rosa hybrida* Grandiflora rose plant was created by artificial pollination wherein two parents were crossed which previously had been studied in the hope that they would contribute the desired characteristics. The female parent (i.e., the seed parent) of the new variety was the 'Sterling Silver' variety (U.S. Plant Pat. No. 1,433). The male parent (i e., the pollen parent) was the 'Silver Spoon' variety (non-patented in the United States). The parentage of the new variety can be summarized as follows:

'Sterling Silver'×'Silver Spoon'.

The seeds resulting from the above pollination were sown and small plants were obtained which were physically and biologically different from each other. Selective study resulted in the identification of a single plant of the new variety.

It was found that the new variety of Grandiflora rose plant of the present invention possesses the following combination of characteristics:

(a) exhibits a bushy and well balanced growth habit,
(b) forms attractive double blossoms that are light to medium lavender in coloration,
(c) forms medium green semi-glossy foliage,
(d) exhibits good disease resistance, and
(e) is particularly well suited for growing as attractive ornamentation.

The new variety well meets the needs of the horticultural industry and can be grown to advantage for cut flower production, as a specimen plant, or in a mass planting.

The new variety of the present invention can be readily distinguished from its ancestors. More specifically, the new variety is Grandiflora rose plant that forms medium to light lavender blossoms having approximately 30 petals on average and no fragrance. The 'Sterling Silver' variety is a Hybrid Tea that forms lilac-colored blossoms having an intense citrus/fruity fragrance. The 'Silver Spoon' variety also is a Hybrid Tea and forms blossoms of a mauve blend having approximately 35 petals on average.

The new variety has been found to undergo asexual propagation by a number of routes, including budding, grafting, and cuttage. Asexual propagation by the above-mentioned techniques at Wasco, Calif. has shown that the characteristics of the new variety are stable and are strictly transmissible by such asexual propagation from one generation to another.

The new variety has been named the 'Wezlavn' variety. The new variety is being marketed under the SILVER STAR trademark.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were three years of age and were observed during the fall while growing outdoors on their own roots at Wasco, Calif. Dimensions in inches and centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimens of leaves with three-leaflets—plan view—upper surface (left) and—under surface (right);

FIG. 13—illustrates specimens of leaves with five leaflets—plan view—upper surface (left) and—under surface (right);

FIG. 14—illustrates specimens of leaves with seven leaflets—plan view—upper surface (left) and—under surface (right);

FIG. 15—illustrates specimens of maturing petals with the under surface at the left and the upper surface at the right;

FIG. 16—illustrates a portion of a flowering stem; and

FIG. 17—illustrates a portion of a current-season mature stem.

DETAILED DESCRIPTION

The chart used in the identification of the colors is that of The Royal Horticultural Society (R.H.S. Colour Chart—1986). The description is based on the observation of two year-old plants during October while growing on their own roots outdoors at Wasco, Calif. Color terminology is to be accorded its ordinary dictionary significance.

Class: Grandiflora.

Plant:

*Height.*—Approximately 4 to 5 feet at the end of the growing season.

*Width.*—Approximately 2 feet at the end of the growing season.

*Habit.*—Bushy and well balanced.

Branches:

*Color.*—Young stems: Yellow-Green Group 144B with highlights of Greyed-Purple Group 184C. Adult wood: Yellow-Green Group 146B.

*Diameter.*—Stems commonly are approximately 9 to 11 mm in diameter at the end of the growing season.

*Thorns.*—Size: approximately 1 cm in length on average. Quantity: moderately numerous, approximately 20 true thorns on a stem having a length of 30 cm. Color: near Greyed-Purple Group 184B. Shape: nearly straight to slightly convex on the upper side and concave on the under side.

Leaves:

*Stipules.*—Narrow, triangular, and with auricle facing outwards.

*Petioles.*—Upper surface: Yellow-Green Group 144C, commonly with scattered minute stiff glandular hairs. Under surface: Yellow-Green Group 144A, and typically glabrous though rarely with an occasional prickle that is up to approximately 3 mm in length.

*Rachis.*—The upper surface commonly is glabrous or may have some scattered minute stiff glandular hairs, and the lower surface typically is glabrous and may occasionally bear 2 to 3 prickles per leaf having lengths up to approximately 3 mm.

*Leaflets.*—Number: 3, 5, and 7. Shape: ovate with serrate margins, rounded base and acuminate apices. Size: the terminal leaflets commonly are approximately 46 to 65 mm (average approximately 56 mm) in length, and approximately 36.5 to 53 mm (average approximately 43 mm) in width. Serration: regular. Texture: glabrous and glaucescent for both young and mature leaves. General appearance: medium green with a semi-glossy finish. Color (young foliage): Upper surface: Green Group 138A with highlights of Red Group 53A. The new plant growth is deep burgundy in coloration. Under surface: Green Group 138B with highlights of Greyed-Purple Group 185B. Color (adult foliage): Upper surface: Green Group 139A with some presence of Green Group 143A. Under surface: Green Group 138B. Venation pattern: pinnately reticulated. Venation color: on the upper surface near Yellow-Green Group 144C, and on the lower surface near Greyed-Green Group 193A.

Inflorescence:

*First bud burst.*—Commonly near April 15th.

*Number of flowers.*—Commonly two to five flowers per stem.

*Flowering duration.*—More or less continuously, though the number of open flowers on the plant may vary throughout the season.

*Peduncle.*—Yellow-Green Group 144B with prickles near Greyed-Purple Group 185B, approximately 3 to 4 mm in diameter, and the length is approximately 5 to 8 cm on average.

*Sepals.*—Upper surface: near Yellow-Green Group 144A and 144B. Under surface: Yellow-Green Group 144A with highlights of Greyed-Purple Group 185B. Number: five. Size: commonly approximately 26 to 37 mm (average approximately 31 mm) in length, and approximately 9 to 11 mm (average approximately 9.6 mm) in width at the widest point.

*Buds.*—Shape: ovoid. Size: large. Length: approximately 3 cm on average. Diameter: approximately 1.5 cm when sepals first separate. Color upon opening: Upper surface: Red-Purple Group 63A and 63B. Under surface: Greyed-Purple Group 186C.

*Flower.*—Shape: double and cup shaped with a flattened center. Diameter: approximately 10 cm on average. Color (when opening begins): Upper surface: Greyed-Purple Group 186C. Under surface: Red-Purple Group 63B and 63C. Color (when blooming): Upper surface: Red-Purple Group 70B and 70C. Under surface: Greyed-Purple Group 186C. Color (at end of opening): Upper surface: Red-Purple Group 69B. Under surface: Red-Purple Group 69A with highlights of Red-Purple Group 70D. Petal shape: generally heart-shaped. Petal margin: undulate towards the apex. Petal apex: broadly obtuse to broadly acute to apiculate, and rarely emarginate. Petal base: broadly cuneate. Petal texture: glabrous. Petal number: approximately 30 on average. Flower longevity: a typical flower commonly lasts approximately 14 to 17 days from bud crack to petal drop on the plant, and approximately 6 to 8 days when cut and placed in a vase. Fragrance: none. Stamen number: approximately 70 on average. Anthers: Greyed-Orange Group 163B in coloration. Filaments: Yellow Group 12C in coloration. Pistils: approximately 35 on average. Stigmas: near Yellow-White Group 158B in coloration. Styles: near Yellow-Orange Group 11B in coloration. Receptacle: separate and free with achenes on the bottom and the wall. Hips: none observed during observations to date.

Development:

*Vegetation.*—Vigorous and strong.

*Blooming.*—Substantially continuous throughout the season.

*Resistance to diseases.*—Very good.

*Hardiness.*—Performs well in U.S.D.A. Hardiness Zone No. 7. With some protection can be grown in Zone No. 6.

*Drought tolerance.*—Believed to be typical of other Grandiflora and Hybrid Tea Rose plants with no significant drought tolerance having been observed.

*Heat tolerance.*—Does well under high heat conditions and is believed to tolerate heat better than typical Grandiflora rose varieties.

Plants of the 'Wezlavn' variety have not been observed while being grown under all possible environmental conditions. Thus, the phenotypic expression may vary somewhat with different light intensity and duration, and different cultural and environmental conditions.

I claim:

1. A new and distinct variety of Grandiflora rose plant characterized by the following combination of characteristics:

(a) exhibits a bushy and well balanced growth habit, (b) forms attractive double blossoms that are light to medium lavender in coloration, (c) forms medium green semi-glossy foliage, (d) exhibits good disease resistance, and (e) is particularly well suited for growing as attractive ornamentation;

substantially as herein shown and described.

* * * * *

'WEZLAVN'